United States Patent [19]
Rechtin

[11] Patent Number: 5,894,015
[45] Date of Patent: Apr. 13, 1999

[54] DISINFECTION OF MEDICAL SHARPS

[76] Inventor: Michael D. Rechtin, 9080 N. Greenbrook Ct., River Hills, Wis. 53217

[21] Appl. No.: 08/045,323

[22] Filed: Apr. 7, 1993

[51] Int. Cl.$^6$ .................. A61L 2/18; A61M 5/32
[52] U.S. Cl. ............... 422/301; 422/292; 604/198; 604/199; 604/195
[58] Field of Search ............ 604/198, 199, 604/216, 263, 905, 195; 128/919; 422/292, 301

[56] References Cited

U.S. PATENT DOCUMENTS

| | | | |
|---|---|---|---|
| 3,134,380 | 5/1964 | Armao | 604/199 X |
| 3,587,575 | 6/1971 | Lichtenstein | 604/199 X |
| 4,416,663 | 11/1983 | Hall | 604/199 X |
| 4,801,295 | 1/1989 | Spencer | 604/199 X |
| 4,887,998 | 12/1989 | Martin et al. | 604/110 |
| 4,894,054 | 1/1990 | Miskinyar | 604/136 |
| 4,911,693 | 3/1990 | Paris | 604/192 |
| 4,921,490 | 5/1990 | Spier et al. | 604/192 |
| 4,921,491 | 5/1990 | Champ | 604/199 |
| 4,932,940 | 6/1990 | Walker et al. | 604/110 |
| 5,024,326 | 6/1991 | Sandel et al. | 206/366 |
| 5,112,316 | 5/1992 | Venturini | 604/195 |
| 5,163,908 | 11/1992 | Lambert | 604/198 X |
| 5,188,614 | 2/1993 | Hart | 604/198 X |
| 5,195,983 | 3/1993 | Boese | 604/198 X |

*Primary Examiner*—Robert J. Warden
*Assistant Examiner*—E. Leigh McKane
*Attorney, Agent, or Firm*—Michael D. Rechtin; Foley & Lardner

[57] ABSTRACT

An article of manufacture for disinfecting a medical sharp. A disinfectant housing is integrally coupled to a syringe housing having a needle. The disinfectant housing includes a disinfectant reservoir for holding disinfectant and a reservoir sleeve which is displaceable after use of the syringe to enclose the tip of the needle and apply disinfectant to the needle which remains in a fixed position relative to the syringe housing before and after use.

12 Claims, 5 Drawing Sheets

DISINFECTION OF MEDICAL SHARPS

The present invention is generally concerned with a method and article of manufacture for disinfecting used medical sharps. More particularly, the invention is concerned with a disinfectant formulation comprised of a disinfectant solution which can be disposed on the surfaces of a magnetized medical sharp for providing persistent and thorough disinfection of used medical sharps.

Used medical sharps, such as disposable syringes and disposable surgical tools, have become a major environmental problem as well as a source of spreading deadly diseases, such as HIV and infectious hepatitis. When needles and other medical sharps have been used, they present a substantial danger to medical personnel and disposal workers until the sharps are destroyed. For example, for syringes and IV devices inadvertent needle sticks can and do frequently occur during use of the medical sharp. Such accidents also occur after use during attempts to recap needles and also during disposal of sharps by the health worker. Furthermore, during the collection of refuse which contains needles or other sharps, the workers involved may be exposed to uncovered needles or exposed needles, such as sharps protruding through refuse containers. The Occupational Safety and Health Administration has on Dec. 6, 1991 issued final rules entitled "Occupational Exposure to Bloodborne Pathogens." These rules are intended to implement standards for reducing the risk to health workers from such contaminated medical sharps. The final rules clearly demonstrate the substantial risks to health workers. For example, the actual observed rate of needlesticks to a worker per 1000 HIV infected patient days was 1.9. Thus, for 45,000 patient days for HIV infected patients, the expected number of needlesticks is 86. Considering current projections of nearly one million HIV infected persons by the year 2000 and their need for health care, the potential for unwanted transmission of HIV is substantial and clearly requires implementation of safety measures to reduce risk to health workers. Of particular importance is the data from the OSHA ruling which notes that of 1,201 actual exposures by health workers to HIV, 17% of these exposures arose from improper recapping of needles immediately after use and 14% of these exposures resulted from sharps which were improperly disposed of after use. In addition, another study showed another 12.3% cases of accidental sticks from sharps arose from needles piercing caps upon recapping the needles after use. The largest number of cumulative exposures to HIV arise from disposable syringes due to the enormous frequency of their use. The largest per incident risk arises from intravenous needle assemblies in which the risk of exposure was 36.7 per 100,000 uses (about a five times greater level of risk than for disposable needles, but of course were used less frequently).

A variety of techniques and devices have been developed to reduce these risks, including: (a) medical waste disposal canisters with and without chemical disinfectants, (b) syringes which automatically recap syringe needles after use, (c) disposal containers constructed to safely hold used medical sharps and (d) devices which obliterate used medical sharps by grinding, crushing or ultra high temperature incineration. None of these methods, however, solve the problem of disinfecting the medical sharps immediately after use on a diseased patient, nor provide self-contained persistent disinfection without use of complex mechanisms for retraction of the needle itself.

It is therefore an object of the invention to provide an improved method and article of manufacture for disinfecting medical sharps.

It is a further object of the invention to provide a novel method of disinfecting medical sharps by magnetizing medical sharps for subsequent disinfection by magnetizable disinfectant fluid mixtures.

It is also an object of the invention to provide an improved method and article of manufacture for disinfecting medical sharps using a surfactant activated disinfectant to coat metal surfaces of used medical sharps.

It is still another object of the invention to provide a novel article of manufacture for disinfecting magnetizable medical sharps comprised of a ferrofluid or magnetizable material and disinfectant solution.

It is yet a further object of the invention to provide an improved disposable syringe having a frangible pouch of disinfectant solution releasable upon use of the syringe.

It is an additional object of the invention to provide a novel medical sharps disposal system for magnetizing used medical sharps and imparting a solution of disinfectant and ferrofluid or magnetizable material onto the metallic surface of the used sharp.

It is also another object of the invention to provide an improved disinfectant solution dispersible onto a used, magnetized medical sharp enabling percolation of the solution into the recesses of any such sharp for disinfection.

It is still a further object of the invention to provide a novel use of at least one of a viscous disinfectant solution, a ferrofluid solution or a magnetizable disinfectant solution disposed onto a metal surface allowing retention of at least part of the disinfectant solution on the metal surface.

It is yet an additional object of the invention to provide an improved method and article of manufacture using a magnetic microsphere/disinfectant solution for rendering harmless pathogens on used magnetized medical sharps.

It is still a further object of the invention to provide a novel resilient cover and/or displaceable reservoir attached to a syringe and containing a solution of a disinfectant for destruction of pathogens.

Other objects and advantages of the invention, together with the manner of use, will be more readily understood by reference to the detailed description when considered in conjunction with the following brief description of the drawings.

DETAILED DESCRIPTION OF PREFERRED EMBODIMENTS

Method of Making Magnetizable Disinfectant

Figure 1:
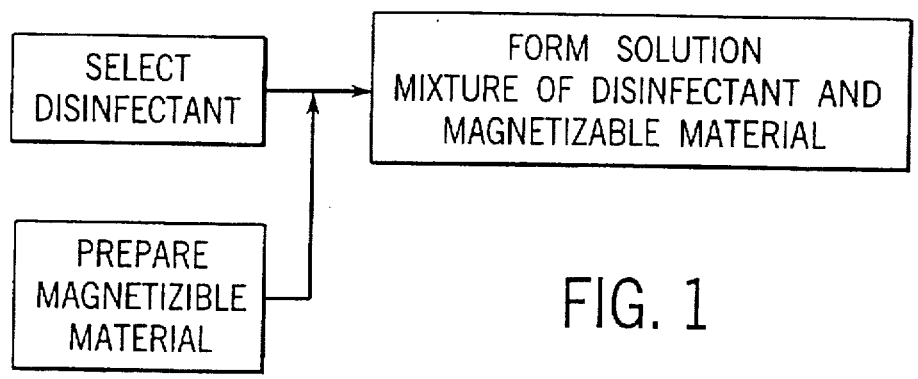
FIG. 1 illustrates by way of a flow diagram a method of making a magnetizable disinfectant as a solution mixture in accordance with the invention.

In one embodiment of the invention, a method of making a magnetizable disinfectant for medical sharps is described in FIG. 1. A magnetizable material forms part of the magnetizable disinfectant and can be prepared by obtaining a fluid containing a powder dispersion of a "magnetic material," such as iron, ferrite or any other conventional material capable of being attracted by a magnet. The fluid powder mixture can then be combined with a conventional disinfectant (such as, for example, a bacteriocide, virucide, a bacteriostatic solution or a virustatic solution) to form a solution mixture. Specific conventional examples of disinfectants include a chloride solution (such as common bleach), an ammonia solution and a glutaraldelyde solution. One can also directly disperse magnetizable material in the disinfectant solution to form the solution mixture for disinfection. The dispersion of magnetizable material enables the solution mixture to coat the magnetized sharp and be strongly retained over a long time period such that the disinfectant can thoroughly eradicate any germs or viruses which might be contaminating the surface of the used magnetized sharp. In the preferred embodiment, the dispersion of magnetizable material acts as a means to provide a cohesive disinfectant coating, wherein surface tension forces cause retention of the disinfectant around the magnetizable material coupled by magnetic forces to the magnetized medical sharp. Preferably the medical sharp is constructed of a material able to be permanently magnetized and produce a magnetic field of strength adequate to retain a substantial amount of the magnetizable material in the disinfectant solution. Such materials for a medical sharp are well known materials, such as conventional iron alloys, like chrome-iron alloys.

In another form of the invention the magnetizable material can comprise a ferrofluid containing extremely fine magnetizable particles (typically less than about one thousand Angstroms diameter), and such ferrofluids are described in detail in U.S. Pat. Nos. 4,604,222 (columns 1–4 in particular) and 4,687,596 (columns 1–4 in particular) which are incorporated by reference herein. As noted therein, a wide variety of oils, esters, alcohols, ethers, fluorocarbons and water based solutions can be used as a carrier to disperse the fine magnetic particles. The ferrofluid can then be mixed with disinfectant which is capable of forming a substantially homogeneous mixture useful as a solution mixture for disinfection. Surfactants can be used in a conventional manner to assure dispersal of the ferrofluid particles in the disinfectant.

In a further form of the invention the magnetizable material can comprise magnetic microspheres as described in U.S. Pat. No. 4,783,336 (in particular, see columns 1–4), which is incorporated by reference herein. These magnetic microspheres can then be combined with the disinfectant to form a substantially uniform solution mixture with the magnetizable material.

The resulting magnetizable solution mixtures can be disposed on the used medical sharps and be retained strongly on the used metal surface, enabling the disinfection of the sharp over a lengthy time period as described hereinbefore. Conventional disinfectants are typically not retained on the surface of medical sharps unless the used medical sharp is totally immersed in disinfectant which is at best impractical under normal conditions of disposal.

Disinfectant/Surfactant Solutions

In addition to the embodiment using magnetizable particles to form a disinfectant solution mixture, another form of the invention concerns use of a solution mixture formed by mixing disinfectants and a surfactant. The resulting solution mixture can be released by various devices described hereinafter to carry out disinfection of the used medical sharp. A variety of conventional surfactants can be used to assure wetting the surface of the medical sharp, such as for example, surfactant/detergent solutions in the form of commercially available viscous liquid detergents. Such conventional liquids have the proper viscosity and surfactants adequate to insure coating of the used medical sharp once the solution mixture comprised of a disinfectant and surfactant is released.

Figure 2:
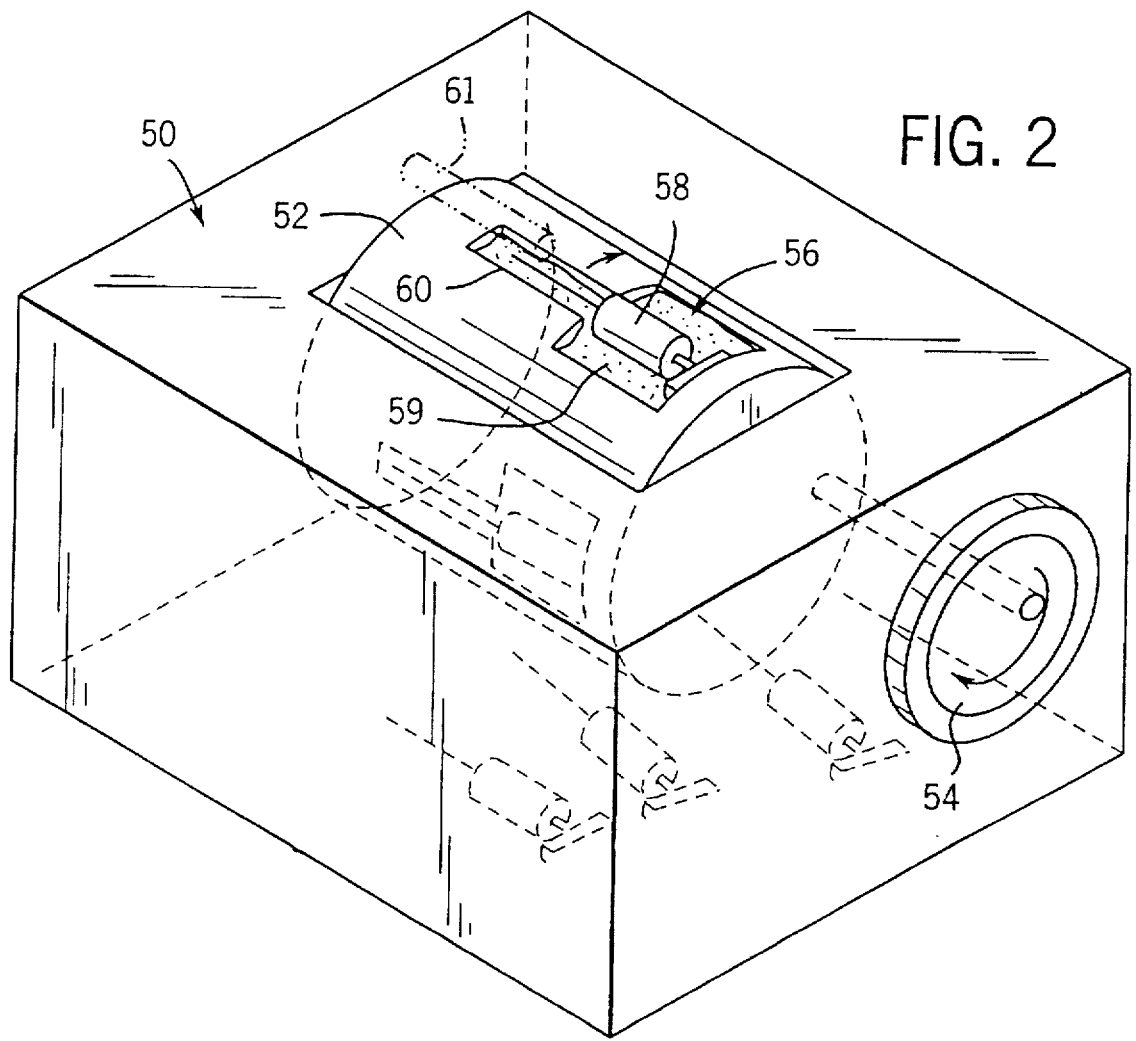
FIG. 2 illustrates a device to contain used medical sharps and for applying a disinfectant solution mixture to sharps.

The solution mixture, either the magnetizable disinfectant or a non-magnetic disinfectant solution with surfactants and of proper viscosity, can be applied to a medical sharp in a variety of ways. In FIG. 2 is illustrated a sharps disposal container 50 with a sharps receptacle drum 52 rotatable using an ordinary hand crank 54. The sharps receptacle drum 52 includes a plurality of concave receptacles 56 for receiving a used medical sharp, such as syringe 58. The concave receptacle 56 includes means for applying the disinfectant solution mixture. Such means can be a foam material 59 or other such porous medium for retaining the solution mixture. In the case of a magnetizable particle/disinfectant, the syringe 58 has a magnetized needle 60 which can attract the magnetizable portion of the solution mixture dispersed in the foam 59. The magnetic forces attract the magnetizable particle of the solution mixture to the needle 60 and surface tension forces retain the disinfectant about the magnetizable particles, thereby coating the needle surface and disinfecting the needle 10. Moreover, the needle 10 will retain the disinfectant for a substantial time period resulting in thorough disinfection of the needle 10.

In other forms of the invention the solution mixture can be dispensed by wiper devices or passed through a bath (not shown) of the solution mixture enroute to a disposal container (not shown). Further, in the system shown in FIG. 2 when the unit is used with a magnetizable disinfectant, a magnet 61 (in phantom) can be used to assure magnetization of the needle 60 or magnetize the needles of syringes not previously magnetized.

Figure 3:
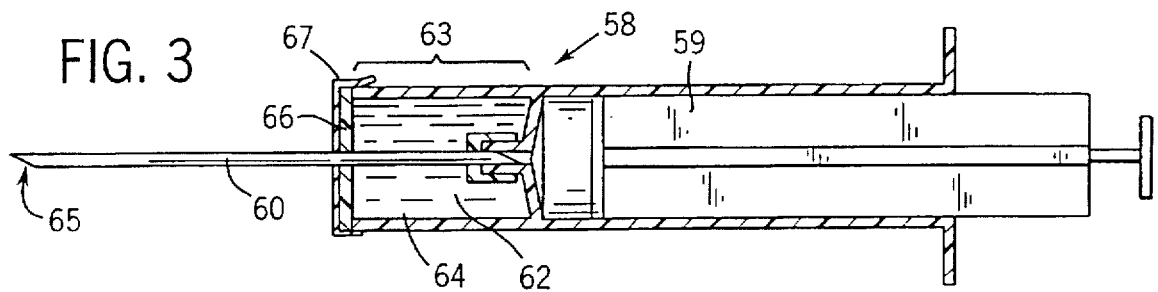
FIG. 3A illustrates a syringe having a frangible reservoir of disinfectant for applying to a needle.

In FIG. 3 is shown another means for applying a solution mixture 62 to the needle 60. A disinfectant housing 63 includes a reservoir 64 which is coupled to syringe housing 59; and the reservoir 64 has a frangible covering 66 which is readily opened by the health care worker using the syringe 58 on the patient. Upon insertion of the needle 60, the force of impact with the patient's skin causes the frangible covering 66 to open and release the solution mixture 62 around the area of needle entry. Alternatively, pull tab 67 is attached to covering 66 and can be removed at any time by the health care worker. Upon removal of the needle 60, the solution mixture 62, which has formed a pool around the entry site of the needle 60, coats the surface of the needle 60. The solution mixture 62 is retained on the surface of the needle 60 and thereby acts to carry out disinfection of the surface of the needle 60 and also disinfect any spurious blood exiting the entry site. In particular, it should be noted that if the syringe 58 were used to draw blood, exposed tip 65 of the needle 60 will likely be a source of ongoing recontamination over a short period of time as fluids percolate out the needle passageway. Conventional disinfection, if done by a technique of a single immersion and removal, will be ineffective. In the instant invention the solution mixture 62 is retained for a relatively long time period and thus alleviates such problems of recurrent contamination.

When using the magnetizable form of the disinfectant solution mixture 62, it has an enhanced attraction (larger field gradient) at the vicinity of the needle tip 65. This strong attraction is due to the steep gradient or concentrated magnetic flux lines at the magnetic pole which is coincident with the needle tip 65. This stronger degree of attraction results in greater quantities of the solution mixture 62 being held at the needle tip 65, thereby providing greater disinfectant action at the location most likely to be responsible for accidental transmission of pathogens to another human.

Figure 5A:
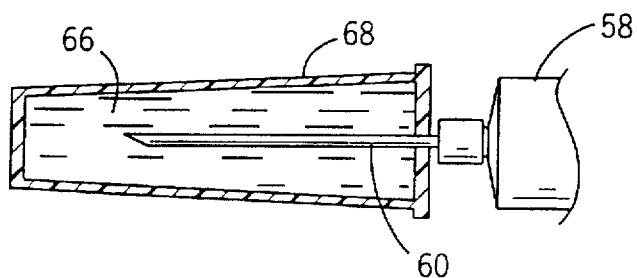
FIG. 5A illustrates a needle cap to contain a disinfectant for application to a used needle.

The solution mixture 62 can also be disposed within a porous matrix (similar to the construction shown in FIG. 2), such as foam 66 disposed within a syringe cap 68 (see FIG. 5A). After being used and upon reinserting the needle 60 in the cap 68, the solution mixture 62 can be applied to the needle 60 to perform disinfection with or without prior application of the solution mixture 62 by other means. Such a syringe cap 68 with included disinfectant solution mixture 62 can be further assurance against transfer of pathogens to refuse workers handling medical refuse downstream in the disposal process.

Figure 4A:
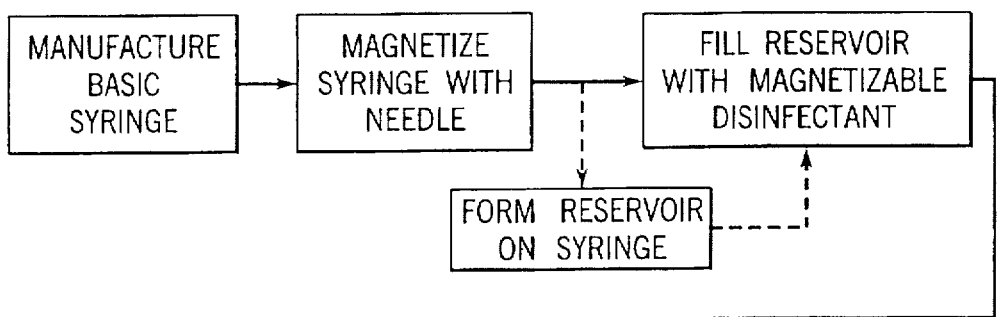
FIG. 4A illustrates a flow diagram of a method of manufacturing a syringe in accordance with one form of the invention.

In another embodiment of the invention a modified syringe can be manufactured and used in the manner of the method described in FIG. 4A. A basic syringe 72 is obtained (see FIG. 4B), and then the needle 74 can be magnetized, such as by a strong permanent magnet or electromagnet. The syringe 72 includes a syringe housing 73 and the disinfectant housing 63 with a coupled reservoir 76 which is preferably integrally formed with the syringe housing 73. The reservoir 76 can be filled in the vertical position with solution mixture 62. A resilient sleeve means (such as plastic bellows 78) is sealingly coupled (such as by heat sealing or other conventional means) to outer surface 80 of the reservoir 76. The plastic bellows 78 includes a cap 82 which is then punctured by the needle 74, and the cap 82 can be preferably sealed onto the shaft of the needle 74 to inhibit leakage of the solution mixture 62. The thickness of the cap 82 is controlled to assure a reasonably good seal to minimize any leakage. The needle 74 is then covered with needle cover 84 for shipment to the end user. This same construction in FIG. 4B can also be used effectively with the needle 74 not being magnetized and the solution mixture 62 being a non-magnetizable disinfectant solution mixture of the type described hereinbefore.

Figure 5B:
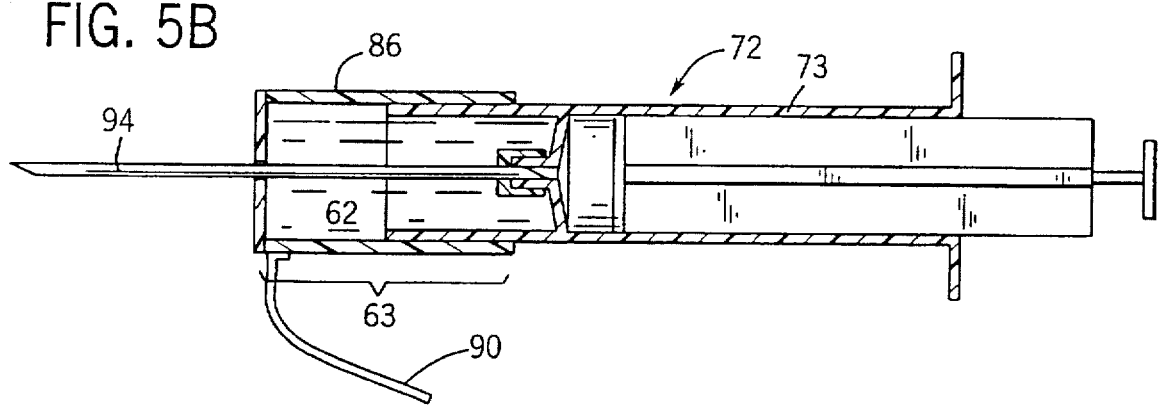
FIG. 5B illustrates a reservoir coupled to a syringe for holding disinfectant solution.

As shown in FIG. 5B, an alternate form of the invention includes a reservoir 86 formed on the syringe 72 by adhesive or heat sealing the reservoir 86 to the syringe housing 73. This alternate method of forming the coupled reservoir 86 and the syringe housing 73 is shown by the phantom lined box in FIG. 4A.

Figure 4B:
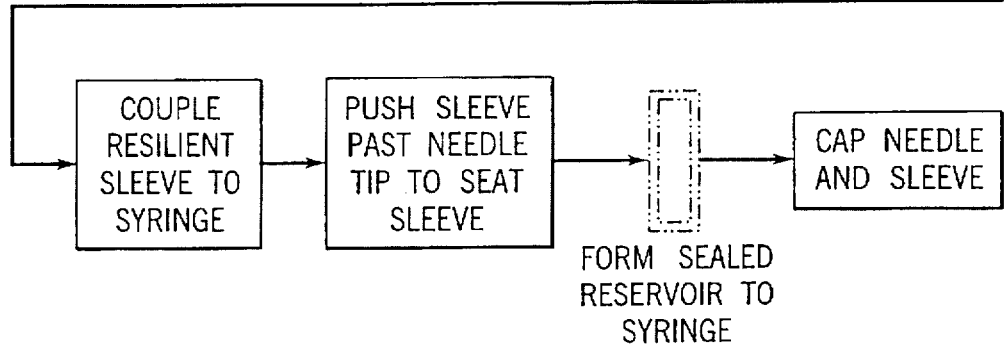
FIG. 4B illustrates a syringe manufactured by the method of FIG. 4A.
Figure 4C:
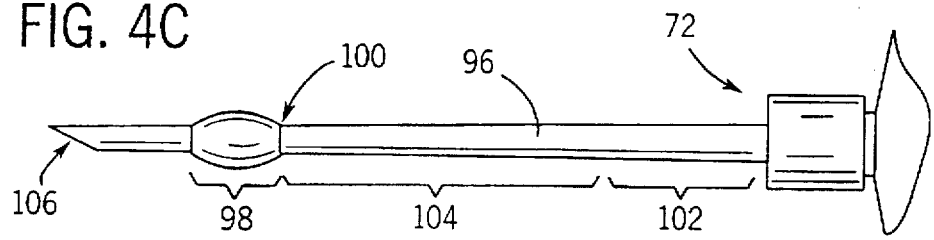
FIG. 4C shows a needle design to assist in sealing the needle of FIG. 4B.

In the device described in FIG. 4B, one can further ensure the sealing of the resilient sleeve means by using a needle 96 shown in FIG. 4C. The profile of the needle 96 is varied by including an enlarged segment 98 to seat the cap 82 by pushing the cap 82 just beyond the segment 98 to position 100. The health worker uses the syringe 72 by inserting the needle 96 into the patient causing the plastic bellows 78 to compress toward shank 102. The needle 96 preferably has an enlarging diameter portion 104, and the displacement of the cap 82 along the needle 96 causes enlargement of the hole in the cap 82. Upon removal of the needle 96 the plastic bellows 78 readily expands to a position beyond tip 106 of the needle 96, thereby substantially enclosing the needle 96.

The solution mixture 62 can then coat and disinfect the entire length of the needle 96.

Figure 5C:
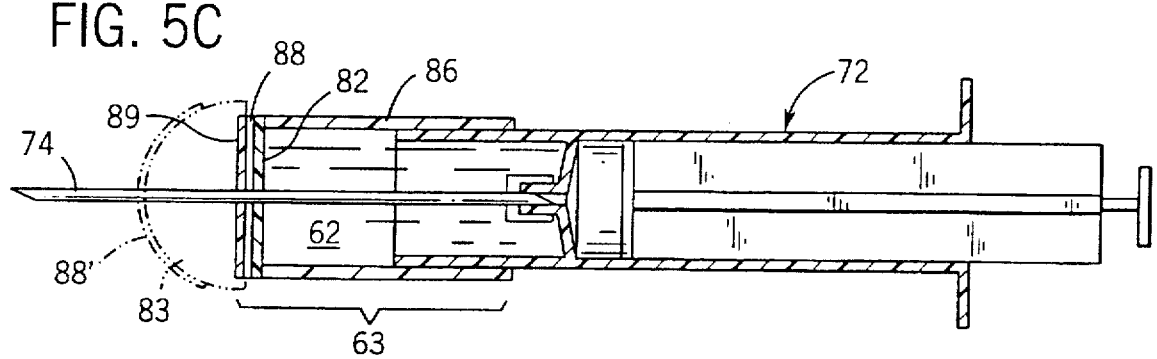
FIG. 5C illustrates yet a further reservoir coupled to a syringe for holding a disinfectant solution.

The cap 82 in FIG. 4B can be integrally formed with the plastic bellows 78 or can be heat sealed or adhesively attached thereto. In addition, an adhesive layer 88 can be disposed on the outer surface of the plastic bellows 78 (see FIG. 4B where the layer 88 is shown dark) or coupled to the reservoir 86 (FIG. 5C). In a conventional manner the adhesive layer 88 can include a protective peel layer 89 (shown as white layer over the layer 88) which can be removed to expose the adhesive. In the embodiment of FIG. 4B the adhesive layer 88 can form a tenuous bond to the patient's skin and thus can assist in assuring full extension of the plastic bellows 78 beyond the tip of the needle 74 to enclose the needle 74 and allow the solution mixture 62 to disinfect the needle 74. In the embodiment of FIG. 5C the adhesive layer 88 also can form an inhibiting seal to the patient's skin to prevent mechanical drainage and loss of the solution mixture 62 before removal of the needle 74 from the patient. In this form of the invention, the solution mixture 62 can thus be more restrained and remain in the near vicinity of the needle entry to be available to disinfect and coat the needle 74 upon withdrawal.

In an alternate form of the embodiment in FIG. 5C, the cap 83 (shown in phantom) can protrude in a convex manner from the reservoir 86. Such a geometry enables the frangible cap 83 to be fractured by impact with the patient upon insertion of the needle 74, enabling dispersion of the disinfectant solution mixture 72 onto the needle 74, as well as disinfection of any body fluids emitted from the entry site. The cap 83 can also include the adhesive layer 88' to perform as described hereinbefore to form a temporary bond to the patient's skin and assist in ensuring disinfectant containment and dispersal on the needle 74 and the area of needle insertion.

In another embodiment of the invention shown in FIG. 5B a release tab 90 enables the health care worker to use the syringe 72; and after usage of the syringe 72, the health worker can remove needle 94 and pull the release tab 90 to allow drainage of the solution mixture 62 onto the needle 94. This form of disinfection can avoid the need to wipe away excess disinfectant from the patient since disinfectant can be released at any time by the health worker. Such a device also causes the health worker to be more aware of the need to be affirmative in completing the disinfection.

Figure 5D:
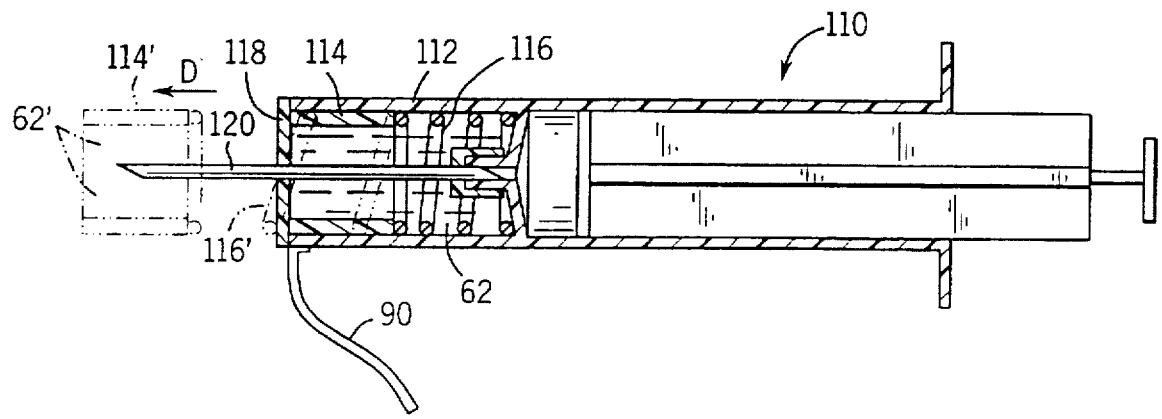
FIG. 5D illustrates a spring loaded reservoir in a syringe for holding a disinfectant solution.
Figure 5E:
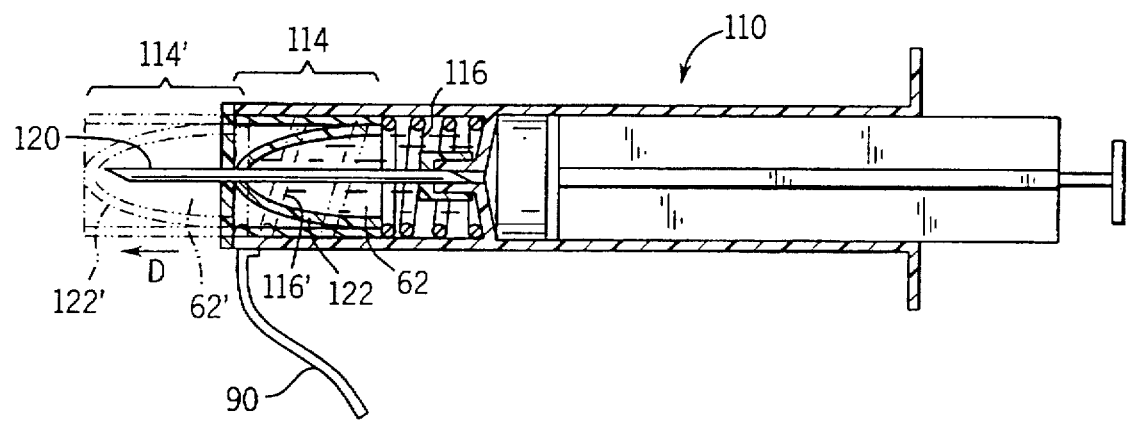
FIG. 5E illustrates yet another type of spring loaded reservoir in a syringe.

In yet another embodiment of the invention shown in FIG. 5D, a syringe 110 includes a reservoir 112 which holds the solution mixture 62 as well as a displaceable reservoir cylinder 114 (shown in cross section in the undisplaced state) and spring 116. A cap 118 forms a seal to needle 120 and also holds the reservoir cylinder 114 against the spring 116 in a compressed state. Upon usage of the syringe 110 the pull tab 90, or other such release device, is used to remove the cap 118 and release the solution mixture 62. Upon removal of the cap 118, the reservoir cylinder 114 moves in the direction of the arrow "D" toward the tip of the needle 120 by virtue of the spring 116 decompressing to state 116'. The solution mixture 62 is then dispersed along the needle 120, and the reservoir cylinder 114 substantially envelopes the needle 120. Note that the elements' positions after displacement are indicated with primed numbers, and this convention is used throughout FIG. 5. A similar form of the embodiment of FIG. 5D is shown in FIG. 5E, but the reservoir cylinder 114 includes interior convexly shaped walls 122 to ensure controlled and thorough dispersion of the solution mixture 62 along the needle 120. Such convexly shaped walls 122 also help reduce potential leakage of the solution mixture 62. Another preferred feature of the embodiment in FIG. 5E is the coupling of the spring 116 to the reservoir cylinder 114 to ensure precise positioning and retention of the reservoir cylinder 114 relative to the needle 120.

Figure 5F:
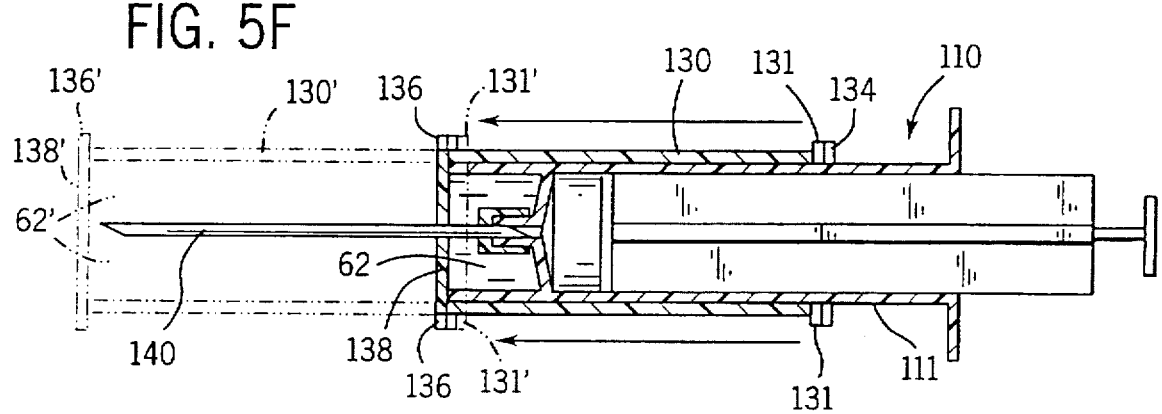
FIG. 5F illustrates a slidable reservoir holding a disinfectant solution.

In another form of the invention shown in FIG. 5F, a reservoir sleeve 130 is slidable along the outer casing of syringe housing 111 between upper stops 134 and lower stop 136. The reservoir sleeve 130 includes upper sleeve stop 131 and lower sleeve stop 136. After usage of the syringe 110, the user can displace the reservoir sleeve 130, fracturing seal cap 138 with needle 140, thereby releasing the solution mixture 62 along the needle 140 (the displaced state of the reservoir sleeve 130' is shown in phantom and element numbers of displaced components are primed as stated hereinbefore).

Figure 5G:
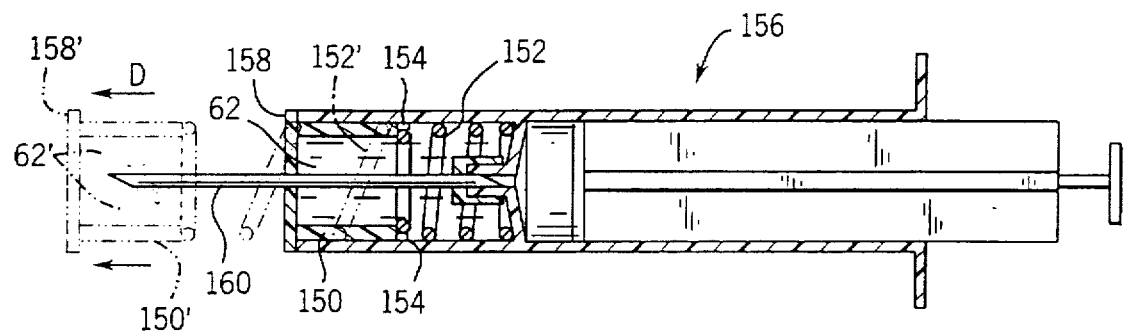
FIG. 5G illustrates still another spring loaded reservoir for a disinfectant solution and actuable by needle insertion into a patient.

In yet another form of the invention shown in FIG. 5G, a reservoir cylinder 150 includes a coupled spring 152 held in the compressed state by a stop 154 in the manner of a conventional ballpoint pen cartridge positioning means. Upon using syringe 156 on the patient, the reservoir cylinder 150 is engaged to the patient's body causing a slight longitudinal retraction, which causes release of the spring 152 past the stop 154, pushing the cylinder 150 causing rupture of the seal formed by cap 158 to needle 160, and displacement of the reservoir cylinder 150 along the direction of the indicated arrow "D" to the position shown in phantom. In this displaced position the needle 160 is coated with the solution mixture 62 after displacement of the reservoir cylinder 150, and the reservoir cylinder 150 substantially encompasses the needle 160 to provide at least a partial physical barrier to contact with the needle 160.

Figure 5H:
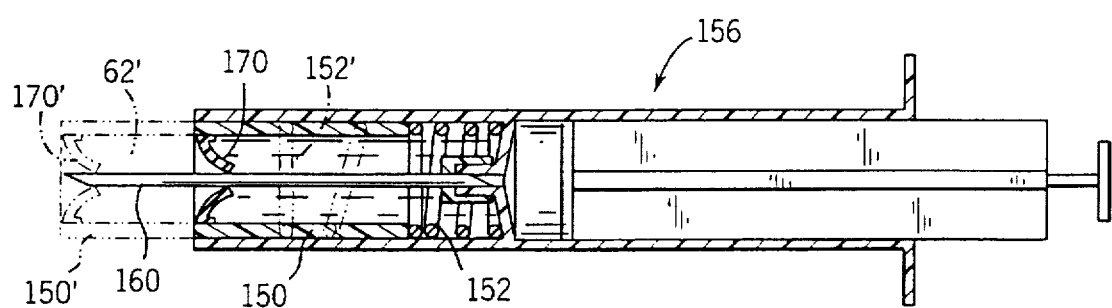
FIG. 5H illustrates an automatic closure valve or shutter valve to assist in shielding the needle from contact after use.

In a variation on the embodiments of FIGS. 5D through 5G, a butterfly style valve or closure shutter 170 can close after sliding past the tip of the needle 160, providing additional protection against inadvertent contact by virtue of someone handling or coming into contact with the syringe 156 (see FIG. 5H). The shutter 170 is shown positioned in a concave orientation but can also be dispersed convexly and cause closure in the intended manner.

The above described features for controlled release of the solution mixture 62 can also be used for "IV" needles and other needle containing fluid removal devices conventional in the health care industry.

While preferred embodiments of the invention have been described, certain aspects of the invention have equivalents known in the art, and it is understood that the scope of the claims provided hereinafter are meant to encompass such equivalents.

What is claimed is:

1. A medical sharp including an article of manufacture for disinfecting the medical sharp after use on a patient, comprising:

the medical sharp having a syringe housing and coupled needle with a tip; and a disinfectant housing means integrally coupled to said syringe housing, said disinfectant housing means for holding disinfectant and including a disinfectant reservoir, a reservoir housing comprised of an inner surface, and a proximal end face and a reservoir sleeve in communication with said disinfectant reservoir, said reservoir sleeve of said disinfectant housing means being initially held fixed apart from the tip before use of said needle and after use of said needle said reservoir sleeve is displaceable away from said syringe housing to at least partially enclose said needle, including the tip, and said disinfectant housing means causing release of said disinfectant to contact said needle and the tip which remain in their fixed positions relative to said syringe housing before and after use of said medical sharp.

2. The article of manufacture as defined in claim 1 wherein said disinfectant housing means further includes seal means openable for allowing release of said disinfectant only after a single use of said medical sharp.

3. The article of manufacture as defined in claim 1 further including spring means for displacing said reservoir sleeve.

4. The article of manufacture as defined in claim 3 wherein said reservoir includes an inner surface and said spring means comprises a mechanical spring disposed between said reservoir sleeve and said proximal end face of said reservoir housing.

5. The article of manufacture as defined in claim 4 wherein said spring means further includes a spring stop means coupled to said disinfectant housing means for maintaining said spring means in a compressed state until use of said needle causes longitudinal retraction of said spring means and subsequent longitudinal extension of said spring means.

6. The article of manufacture as defined in claim 3 wherein said spring means comprises a bellows.

7. The article of manufacture as defined in claim 1 wherein said disinfectant housing means further includes an adhesive sleeve means for at least temporary attachment to the patient upon use of said needle, said adhesive sleeve means also for achieving an inhibiting seal to the patient to prevent drainage and loss of said disinfectant.

8. The article of manufacture as defined in claim 1 wherein said reservoir sleeve includes a convex shaped inner surface means for enhancing retention of said disinfectant about said needle.

9. The article of manufacture as defined in claim 1 wherein said reservoir sleeve is disposed around at least part of the outside surface of said syringe housing.

10. The article of manufacture as defined in claim 1 wherein said disinfectant housing means further includes a closure shutter to cooperate with said reservoir sleeve to cover said needle.

11. The article of manufacture as defined in claim 1 wherein said reservoir sleeve includes the disinfectant contained therewithin said sleeve prior to use of said medical sharp.

12. An article of manufacture for disinfecting a medical sharp for use on a patient, comprising:

a medical sharp having a syringe housing and coupled needle with a tip; and a disinfectant housing means integrally coupled to said syringe housing, said disinfectant housing means for holding disinfectant and including a disinfectant reservoir and a reservoir sleeve in communication with said reservoir, said reservoir sleeve of said disinfectant housing means being initially held fixed apart from the tip before use of said needle and after use of said needle said reservoir sleeve is displaceable away from said syringe housing to at least partially enclose said needle, including the tip, and said needle and the tip remain in their fixed positions relative to said syringe housing before and after use of said medical sharp.

* * * * *